US010960384B2

(12) United States Patent
Jo et al.

(10) Patent No.: US 10,960,384 B2
(45) Date of Patent: Mar. 30, 2021

(54) DEHYDROGENATION CATALYST

(71) Applicant: HYOSUNG CHEMICAL CORPORATION, Seoul (KR)

(72) Inventors: Bu Young Jo, Anyang-si (KR); Won Il Kim, Seongnam-si (KR)

(73) Assignee: HYOSUNG CHEMICAL CORPORATION, Seoul (KR)

( * ) Notice: Subject to any disclaimer, the term of this patent is extended or adjusted under 35 U.S.C. 154(b) by 0 days.

(21) Appl. No.: 15/762,666

(22) PCT Filed: Feb. 6, 2018

(86) PCT No.: PCT/KR2018/001532
§ 371 (c)(1),
(2) Date: Mar. 23, 2018

(87) PCT Pub. No.: WO2018/097701
PCT Pub. Date: May 31, 2018

(65) Prior Publication Data
US 2019/0232255 A1  Aug. 1, 2019

(30) Foreign Application Priority Data
Feb. 1, 2018  (KR) .................. 10-2018-0012719

(51) Int. Cl.
*B01J 21/04* (2006.01)
*B01J 21/06* (2006.01)
(Continued)

(52) U.S. Cl.
CPC ............... *B01J 23/58* (2013.01); *B01J 21/04* (2013.01); *B01J 21/063* (2013.01); *B01J 21/066* (2013.01);
(Continued)

(58) Field of Classification Search
CPC ........ B01J 21/04; B01J 21/063; B01J 21/066; B01J 21/08; B01J 21/12; B01J 23/58;
(Continued)

(56) References Cited

U.S. PATENT DOCUMENTS 4,094,821 A * 6/1978 McVicker ................ B01J 23/58
502/328
4,914,075 A * 4/1990 Bricker .................... B01J 23/58
502/328
(Continued)

FOREIGN PATENT DOCUMENTS

JP         2013-203646    10/2013
KR    10-2010-0078460     7/2010
(Continued)

OTHER PUBLICATIONS

International Search Report, issued in the corresponding PCT Application No. PCT/KR2018/001532, dated Nov. 14, 2018, 5 pages.

*Primary Examiner* — Cam N. Nguyen
(74) *Attorney, Agent, or Firm* — Hamre, Schumann, Mueller & Larson, P.C.

(57) ABSTRACT

The present invention relates to a dehydrogenation catalyst in which a platinum-group metal, an assistant metal, and an alkali metal or alkaline earth metal component are supported on a carrier, wherein the molar ratio of platinum to the assistant metal is 0.5 to 1.49, and the catalyst has an acidity amount of 20 to 150 μmol KOH/g catalyst when it is titrated with KOH. The dehydrogenation catalyst according to the present invention may prevent coke formation from increasing rapidly when the hydrogen/hydrocarbon ratio in a dehydrogenation reaction is reduced, thereby increasing the productivity of the process. Accordingly, it makes it possible to operate the process under a condition in which the hydrogen/
(Continued)

hydrocarbon ratio in a dehydrogenation reaction is reduced, thereby improving the economy of the process.

13 Claims, 1 Drawing Sheet

(51) Int. Cl.
| | | |
|---|---|---|
| *B01J 21/08* | (2006.01) | |
| *B01J 23/58* | (2006.01) | |
| *B01J 23/62* | (2006.01) | |
| *B01J 35/00* | (2006.01) | |
| *B01J 35/02* | (2006.01) | |
| *B01J 35/10* | (2006.01) | |
| *C07C 5/32* | (2006.01) | |
| *C07C 5/333* | (2006.01) | |

(52) U.S. Cl.
CPC ............... *B01J 21/08* (2013.01); *B01J 23/62* (2013.01); *B01J 35/00* (2013.01); *B01J 35/0026* (2013.01); *B01J 35/02* (2013.01); *B01J 35/10* (2013.01); *B01J 35/1014* (2013.01); *B01J 35/1019* (2013.01); *B01J 35/1033* (2013.01); *B01J 35/1066* (2013.01); *C07C 5/325* (2013.01); *C07C 5/3337* (2013.01); *B01J 2523/11* (2013.01); *B01J 2523/12* (2013.01); *B01J 2523/13* (2013.01); *B01J 2523/21* (2013.01); *B01J 2523/22* (2013.01); *B01J 2523/23* (2013.01); *B01J 2523/24* (2013.01); *B01J 2523/25* (2013.01); *B01J 2523/26* (2013.01); *B01J 2523/56* (2013.01); *C07C 2521/04* (2013.01); *C07C 2523/04* (2013.01); *C07C 2523/62* (2013.01)

(58) Field of Classification Search
CPC ........ B01J 23/62; B01J 35/00; B01J 35/0026; B01J 35/02; B01J 35/10; B01J 35/1014; B01J 35/1019; B01J 35/1033; B01J 35/1066; C07C 5/325; C07C 5/3337
See application file for complete search history.

(56) References Cited

U.S. PATENT DOCUMENTS

| | | | | |
|---|---|---|---|---|
| 5,358,920 | A * | 10/1994 | Ma | B01J 23/626 502/330 |
| 6,162,758 | A * | 12/2000 | Brooker | B01J 23/06 502/340 |
| 7,087,802 | B2 * | 8/2006 | Schindler | B01J 38/14 585/660 |
| 8,993,474 | B2 * | 3/2015 | Choi | B01J 23/58 502/213 |
| 9,266,091 | B2 * | 2/2016 | Serban | B01J 27/10 |
| 9,669,395 | B2 * | 6/2017 | Hung | B01J 23/6522 |
| 2002/0022755 | A1 | 2/2002 | Dongara | B01J 23/8966 585/661 |
| 2005/0033101 | A1 * | 2/2005 | Voskoboynikov | B01J 21/04 585/660 |
| 2006/0067877 | A1 * | 3/2006 | Revel | B01J 21/04 423/628 |
| 2008/0051618 | A1 * | 2/2008 | Kim | B01J 23/62 585/431 |
| 2010/0087694 | A1 * | 4/2010 | Mishima | B29C 48/91 585/661 |
| 2015/0202601 | A1 | 7/2015 | Luo et al. | |
| 2017/0021341 | A1 * | 1/2017 | Mandan | B01J 37/0203 |

FOREIGN PATENT DOCUMENTS

| | | |
|---|---|---|
| KR | 10-2010-0078465 | 7/2010 |
| KR | 10-2011-0078818 | 7/2011 |
| KR | 10-2012-0077688 | 7/2012 |
| KR | 10-2014-0123929 | 10/2014 |

* cited by examiner

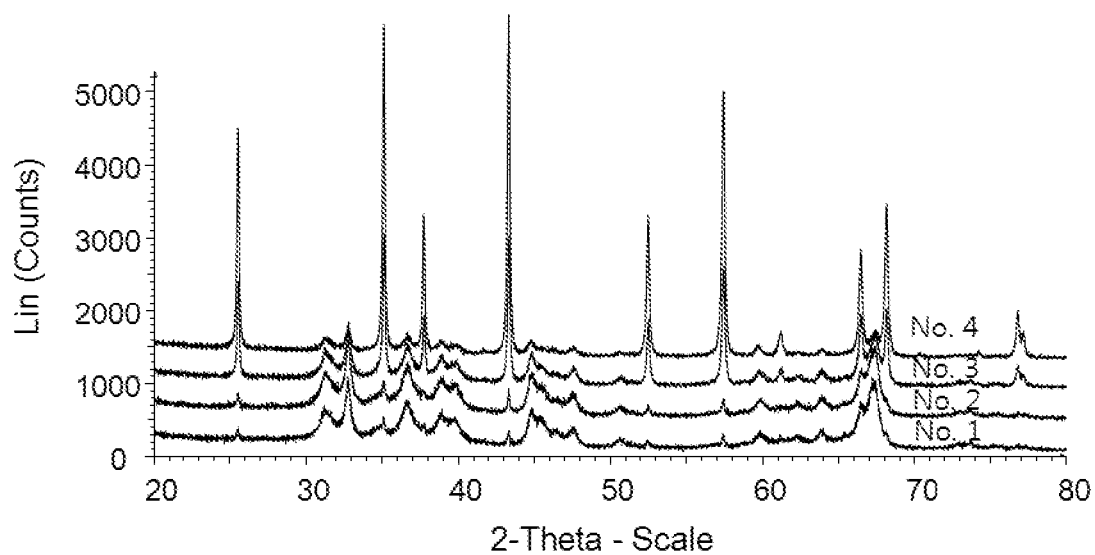
|  | No. 1 | No. 2 | No. 3 | No. 4 |
| --- | --- | --- | --- | --- |
| Calcination temperature (℃) | 1,060 | 1,080 | 1,090 | 1,100 |
| Calcination time (hrs) | 2 | 2 | 2 | 2 |
| θ : α ratio | 97 : 3 | 94 : 6 | 61 : 39 | 25 : 75 |

DEHYDROGENATION CATALYST

TECHNICAL FIELD

The present invention relates to a catalyst which is used for the dehydrogenation of hydrocarbons, and more specifically to a dehydrogenation catalyst exhibiting a low molar ratio of platinum and a reduced acidity amount, which reduces coke, thereby improving the long-term operating performance of the catalyst, and which enables a dehydrogenation process to be operated under a condition in which the hydrogen ratio is reduced, thereby improving the yield of the process.

BACKGROUND ART

The catalytic dehydrogenation of alkanes used to produce alkenes (olefin hydrocarbons) is an important and well-known hydrocarbon conversion process in the petroleum refining industry. The reason for this is that alkenes are generally useful as intermediates in the production of other more valuable hydrocarbon conversion products. For example, propylene can be used in the production of polymers and propylene glycol, butylene can be used in the production of high-octane motor fuel, and isobutylene can be used to produce methyl-t-butyl ether, a gasoline additive.

Dehydrogenation of hydrocarbon gases, such as the catalytic dehydrogenation of alkanes, is carried out at a high temperature of 550° C. or above. Since the catalytic reaction is carried out at high temperatures, it is accompanied by side reactions, such as thermal decomposition and coke formation. The extent of such side reactions becomes an important factor that determines catalytic selectivity and activity. Coke formation which is a side reaction causes an active catalytic material to be covered with coke, which blocks its contact with a reactant, thereby decreasing the total conversion of the reactant. Furthermore, as coke formation occurs, it blocks the entrance of pores in the catalyst, thereby accelerating the deactivation of the active material in the pores.

U.S. Patent Application Publication No. 2015/0202601 A1 discloses an alkane dehydrogenation catalyst composition including: a Group IIIA metal selected from gallium, indium, thallium, and combinations thereof; a Group VIII noble metal selected from platinum, palladium, rhodium, iridium, ruthenium, osmium, and combinations thereof; at least one dopant selected from iron, chromium, vanadium, and combinations thereof; an optional promoter metal selected from sodium, potassium, rubidium, cesium, magnesium, calcium, strontium, barium, and combinations thereof; and a catalyst support selected from silica, alumina, silica-alumina composites, rare earth modified alumina, and combinations thereof.

Korean Patent Application Publication No. 2014-0123929 discloses a dehydrogenation catalyst composition for hydrocarbons, including: a nano-sized complex containing a Group VIII component; a group IVA component and a sulfur-containing capping agent; an alkali component; a halogen component; and a support having an inner core of alpha alumina and an outer layer including a mixture of gamma alumina and delta alumina.

Conventionally known patents related to dehydrogenation catalysts are directed mainly to the types of active catalytic components and supports, and there is still no content related to acidity amount which is one of the physical properties of catalysts. Therefore, there is an urgent need to develop a dehydrogenation catalyst which has an acidity amount within an appropriate range and which is excellent in terms of catalytic activity, selectivity, and stability against coke formation.

DISCLOSURE

Technical Problem

The present applicant has found that when the molar ratio of platinum to an assistant metal in a catalyst is lowered, the promoting effect of platinum and the assistant metal can be optimized, thereby improving the operating performance of the catalyst. Furthermore, when the acidity amount of the catalyst is controlled within a specific range, a dehydrogenation process can be performed under a condition in which the hydrogen/hydrocarbon ratio is reduced, thereby significantly improving the yield of the process. In particular, the present applicant has found that a catalyst having an acidity amount within the scope of the present invention provides lower coke formation, better long-term stability, or higher activity.

An object of the present invention is to provide a dehydrogenation catalyst useful for the dehydrogenation of hydrocarbons, which has a low molar ratio of platinum and a predetermined acidity amount.

Another object of the present invention is to provide a catalyst suitable for dehydrogenation, which enables increased long-term operating performance, low coke formation, and excellent process yield.

Yet another object of the present invention is to provide a dehydrogenation method which achieves the increased long-term operating performance of a catalyst, low coke formation, and excellent process yield.

Technical Solution

One aspect of the present invention for achieving the above objects is directed to a dehydrogenation catalyst in which a platinum-group metal, an assistant metal, and an alkali metal or alkaline earth metal component are supported on a carrier, wherein the molar ratio of platinum to the assistant metal is 0.5 to 1.49, and the catalyst has an acidity amount of 20 to 150 μmol KOH/g catalyst when it is titrated with KOH.

The catalyst includes, based on the total weight of the catalyst, 0.3 to 0.8 wt % of platinum and 0.4 to 0.9 wt % of the alkali metal or alkaline earth metal which are supported on the carrier.

The catalyst has a bulk density of 0.55 to 0.9 g/cc and a pill size of 1.2 to 2.5 mm.

The carrier of the catalyst has a bimodal pore size distribution including both mesopores having an average pore size of 5 to 100 nm and a total pore volume of 0.05 to 2 cm$^3$/g and macropores having an average pore size of 0.1 to 20 μm and a total pore volume of 0.05 to 3 cm$^3$/g.

Advantageous Effects

According to the present invention, the molar ratio of platinum to an assistant metal in a dehydrogenation catalyst is lowered, so that the promoting effect of the assistant metal and platinum may be optimized to increase the yield of propylene, and so that coke formation may be reduced to improve the long-term operating performance of the catalyst.

The dehydrogenation catalyst according to the present invention may provide high hydrocarbon conversion and selectivity, high performance and stability, improved resistance to coke formation, and easy coke removal.

Furthermore, according to the present invention, the acidity amount of the dehydrogenation catalyst is controlled within a specific range to make it possible to prevent coke formation from increasing rapidly when the hydrogen/hydrocarbon ratio in a hydrogen dehydrogenation reaction is reduced. Accordingly, it makes it possible to operate the process under a condition in which the hydrogen/hydrocarbon ratio is reduced, so that the productivity of the process is increased, thereby improving the economy of the process.

The catalyst according to the present invention has an increased bulk density, so that the mass of catalyst introduced per unit reactor volume may increase and thus the performance of the reactor may be improved, thereby improving the yield of the process.

DESCRIPTION OF DRAWINGS

FIG. 1 is a view showing the results of measuring the crystallinity of a catalyst carrier (alumina) according to the present invention by using an X-ray analysis method.

BEST MODE

The present invention will be described in detail below.

It should be noted that the term "including or comprising" or "include or comprise" used herein does not exclude the presence of another element. In the same way, it is also to be understood that the expression "including or comprising certain steps" in a description of a method including certain steps does not exclude the inclusion of another step.

A dehydrogenation catalyst according to one exemplary embodiment of the present invention is a dehydrogenation catalyst in which a platinum-group metal, an assistant metal, and an alkali metal or alkaline earth metal component are supported on a carrier, wherein the molar ratio of platinum to the assistant metal is 0.5 to 1.49, and the catalyst has an acidity amount of 20 to 150 μmol KOH/g catalyst when it is titrated with KOH.

In the present invention, the acidity amount is a measure of the free acid component on the catalyst carrier, and is expressed as the amount of (μmol) of potassium hydroxide (KOH) neutralized by acid sites present in 1 g of the catalyst carrier.

If the acidity amount of the catalyst in the present invention is less than 20 μmol KOH/g, it will be difficult to disperse the metal active phase, due to the insufficiency of acid sites in the catalyst. If the acidity amount is more than 150 μmol KOH/g, the production of methane, ethylene and ethane, which is a side reaction, may be promoted due to the presence of an excessive amount of acid sites in the catalyst to thus reduce selectivity, and these by-products may strongly bond to a reactant or a product to thus increase coke formation which reduces the activity of the catalyst, thereby reducing the performance of the catalyst.

When the hydrogen/hydrocarbon ($H_2$/HC) ratio in hydrocarbon dehydrogenation is reduced, a rapid increase in coke formation appears. However, when the acidity amount of the catalyst is controlled within the above-specified range, it is possible to prevent coke formation from increasing rapidly even when the hydrogen/hydrocarbon ratio is reduced. Accordingly, the use of the catalyst according to the present invention makes it possible to carry out a dehydrogenation process under conditions in which the hydrogen/hydrocarbon ratio is reduced, so that the productivity of the dehydrogenation process is increased, thereby significantly increasing the process yield.

In the present invention, the acidity amount of the catalyst may be controlled by various methods. In the first method, the acidity amount may be reduced by controlling the temperature and time of heat treatment of the catalyst to thermally decompose —OH groups present on the catalyst surface to thus reduce the number of the —OH groups. In the second method, the acidity amount may be reduced by increasing the content of the assistant metal to reduce acid sites on the platinum-group metal and acid sites on the catalyst surface by blocking or alloy formation. However, if the assistant metal is used in an excessive amount, it may cover the surface of the platinum-group metal to thus reduce the performance of the catalyst. For this reason, the assistant metal should be used in a suitable amount. In the third method, the acidity amount of the catalyst may be reduced by increasing the content of the alkali metal or alkaline earth metal to neutralize the residual acid sites of the catalyst. In addition to the three methods, the acidity amount of the catalyst may also change sensitively with a change in the content and ratio of the platinum-group metal, the assistant metal and the alkali metal or alkaline earth metal, and the acidity amount of the catalyst may also be controlled by a method, such as introduction of a fourth new co-catalyst.

The main metal of the catalyst according to the present invention is a platinum-group metal. The platinum-group metal component may include a noble metal component, such as platinum, palladium, ruthenium, rhodium, iridium, or a mixture thereof. The platinum-group metal may exist within the dehydrogenation catalyst as a compound, such as an oxide, a sulfide, a halide, an oxyhalide or the like, in chemical combination with one or more other ingredients of the composite, or as an elemental metal. The platinum component accounts for from 0.3 to 0.8 wt %, calculated on an elemental basis, of the dehydrogenation catalyst.

The dehydrogenation catalyst according to the present invention is a catalyst having a low molar ratio of platinum to the assistant metal. The molar ratio of platinum to the assistant metal in the dehydrogenation catalyst is preferably 0.5 to 1.49. If the molar ratio of platinum to the assistant metal is lower than 0.5, the interaction between the platinum and the assistant metal will decrease, and for this reason, the production of a Pt—Sn alloy having excellent catalytic performance will decrease, resulting in a decrease in the performance of the catalyst. In particular, coke formation will increase, resulting in a decrease in the long-term performance of the catalyst and a decrease in the propylene selectivity of the catalyst. If the molar ratio of platinum to the assistant metal is higher than 1.49, the assistant metal over-supported will cover a portion of the surface of the platinum so that the dehydrogenation activity of the catalyst can be reduced.

The catalyst according to the present invention includes 0.3 to 0.8 wt % of platinum and 0.4 to 0.9 wt % of the alkali metal or alkaline earth metal. If the content of the platinum component is less than 0.3 wt %, the dehydrogenation activity of the catalyst may decrease, and if the content of the platinum component is more than 0.8 wt %, propylene selectivity may be reduced due to the cracking of hydrocarbons by platinum.

Meanwhile, if the content of the alkali metal or alkaline earth metal component is less than 0.4 wt %, the acidity of the carrier may increase so that cracking and coke formation may increase, resulting in a decrease in the selectivity for dehydrogenation, and if the content of the alkali metal or alkaline earth metal component is more than 0.9 wt %, the activity of the catalyst may decrease so that dehydrogenation conversion may decrease.

The catalyst according to the present invention preferably has a bulk density of 0.55 to 0.9 g/cc. The bulk density of the catalyst is a factor that determines the packed amount of the catalyst introduced into a process, thereby determining the total active density of the catalyst introduced into the process. If the bulk density of the catalyst is lower than 0.55 g/cc, process performance may decrease due to a decrease in the mass of catalyst packed into a reactor, and if the bulk density is higher than 0.9 g/cc, the size of pores in the catalyst may become smaller so that the mass transfer resistance of a reactant may increase, resulting in deterioration in the performance of the catalyst.

The catalyst according to the present invention is composed of spherical particles having a pill size of 1.2 to 2.5 mm. Spherical carrier particles may be continuously prepared by the well-known oil-drop method. According to this method, spherical carrier particles may be prepared by any technique known in the art. For example, a spherical alumina catalyst carrier may be prepared by a method which includes: reacting hydrochloric acid with aluminum metal to form an alumina slurry with Ziegler alumina or an alumina hydrosol; combining the resulting hydrosol or slurry with a suitable gelling agent; and dropping the resultant mixture into an oil bath maintained at elevated temperatures. When the droplets of the mixture form spheres, the spheres are then withdrawn and subjected to aging and drying treatments in order to further improve the physical characteristics of the support. Then, the resulting aged and gelled particles are washed and calcined, thereby obtaining a spherical crystalline alumina carrier.

If the pill size of the catalyst is smaller than 1.2 mm, a problem may arise in that coke is formed in the catalyst during a process operation in the reactor catalyst bed to thus rapidly increase the pressure during passage of a reactant. Due to this problem, the life-span of the catalyst can be reduced, or in order to inhibit coke formation, the reaction temperature should be lowered so that the process should be operated under conditions in which the productivity of the process is low. On the contrary, if the pill size of the carrier is larger than 2.5 mm, problems may arise in that the resistance to mass transfer from the surface to the inside of the catalyst occurs to reduce the performance of the catalyst, and in that it is difficult to completely remove coke formed in the catalyst, during catalyst regeneration, and thus a problem in a catalyst regeneration process is caused by coke accumulation in the catalyst.

The assistant metal used may be selected from the group consisting of tin, germanium, gallium, indium, zinc and manganese, and is particularly preferably tin. The alkali metal or alkaline earth metal used may be selected from the group consisting of calcium, potassium, sodium, magnesium, lithium, strontium, barium, radium and beryllium.

The catalyst according to the present invention may further include, based on the total weight of the catalyst, 0.1 to 3.0 wt % of a halogen component. As the halogen component, one selected from the group consisting of chlorine, phosphorus, and fluorine is used, and chloride is particularly preferable. If the content of the halogen is less than 0.1 wt %, the rate of coke formation on the catalyst may increase rapidly, the regeneration of the coked catalyst may decrease, and the dispersion of platinum during catalyst regeneration may decrease. If the content of the halogen is more than 3.0 wt %, the activity of the catalyst may be reduced due to the noble metal poisoning by the halogen.

Namely, the halogen component, particularly chlorine, bonds to the aluminum atom of the alumina carrier to deactivate the Lewis acid of the alumina itself to thus facilitate product desorption, thereby exhibiting the effect of inhibiting coke formation. As such, the coke may be formed in such a way that the reaction is completed with coke adsorbed on the carrier itself or the main product/byproduct formed at the active sites may be spilt-over and deposited on the carrier and additional coke formation reactions occur. However, when the Lewis acid of the carrier is deactivated to facilitate product desorption, the amount of coke deposited on the carrier may decrease so that coke formation may decrease. In addition, the halogen component serves to control the sintering of platinum during regeneration of the catalyst.

The carrier that is used in the catalyst according to the present invention may be selected from the group consisting of $TiO_2$, $SiO_2$, $Al_2O_3$, $ZrO_2$, $Cr_2O_3$, $Nb_2O_5$, and mixtures thereof, and is preferably alumina. The theta crystallinity of alumina is a factor that determines the degree of coke formation. The alumina ($Al_2O_3$) carrier preferably includes 90% to 100% theta-crystalline phase and 0% to 10% alpha-crystalline phase or gamma-crystalline phase. When gamma-alumina is used, side reactions may increase due to acid sites of the alumina itself, and changes in structural properties of the alumina, such as a change in the alumina crystallinity and a decrease in the specific surface area of the alumina, may take place during the reaction. On the other hand, alpha-alumina may decrease the dispersion of noble metals due to its low specific surface area and may reduce the total active area of platinum, leading to low catalytic activity. For these reasons, the alumina carrier preferably has a theta-crystalline phase content of 90% or more.

What are important considerations in the present invention are the size distribution of macropores per unit catalyst weight, the total volume of macropores, the uniform distribution thereof, the size distribution of mesopores in macropores, and the total volume of mesopores. The carrier has a bimodal pore size distribution including both mesopores having an average pore size of 5 to 100 nm and a total pore volume of 0.05 to 2 $cm^3/g$, and macropores having an average pore size of 0.1 to 20 μm and a total pore volume of 0.05 to 3 $cm^3/g$. Due to bimodal pore size distribution characteristics, the catalyst of the present invention shows improved activity in dehydrogenation reactions and easy regeneration.

The pore volume and pore size of the carrier are factors that determine the mass transfer coefficients of reactants and products. In a state in which chemical reaction rates are high, the diffusion resistance of material determines the overall reaction rate. For this reason, a carrier having a large pore size is advantageous for maintaining the activity of the catalyst at a high level. Accordingly, when a carrier having a large pore size is used, it becomes insensitive to the accumulation of coke, and will show a high mass transfer rate, and thus show high reaction activity even at increased liquid hourly space velocity (LHSV). If the pore size of the carrier is smaller than 5 nm, the mass transfer rate will decrease, and the pore size of the carrier is larger than 20 μm, the strength of the carrier will decrease. Namely, when the pore size is smaller than 10 nm, Knudsen diffusion appears, and when the pore size is 10 to 1000 nm, transition diffusion appears, and the pore size is larger than 1000 nm, bulk diffusion appears. Accordingly, a carrier having a macropore size of 1 μm or higher has a mass transfer rate which is at least 20-fold higher than that of a carrier having a pore size of 10 nm. In addition, if the macropore size is excessively large, the surface area capable of supporting a catalytically active material may decrease, and for this reason, the dispersion of the metal may decrease, and thus the performance of the catalyst may decrease. Furthermore, if the pore volume is excessively large, the thickness of walls defining the pores of the catalyst may decrease so that the strength of the catalyst may decrease, and thus a process problem caused by catalyst failure during a process operation may occur.

The carrier has a specific surface area of 50 to 170 m²/g. If the specific surface area of the support is less than 50 m²/g, the dispersion of the active metal component will decrease. If the specific surface area is more than 170 m²/g, the gamma-crystallinity of the alumina will be maintained at a high level to thus increase side reactions.

The catalyst according to the present invention preferably has a strength of 15 to 70N, and may have an increased strength so that it is rigid even when it is regenerated or circulated. If the strength of the catalyst is lower than 15 N, it may easily break down, thereby making it difficult to apply to a continuous reaction system. Since the dehydrogenation catalyst is accompanied by coke formation, it is regenerated by burning coke via oxidation after a predetermined reaction. During this process, thermal breakage may occur. When the catalyst circulates in order to operate, friction or impact may be applied thereto during transport. In the case where a catalyst weak against impact is used, it hinders the flow of the product and increases the inner pressure of the reactor, undesirably lowering catalytic conversion. Hence, the catalyst having high strength is very advantageous in terms of process operation.

The molar ratio of platinum in the dehydrogenation catalyst according to the present invention is reduced to 0.5-1.49, and thus the promoting effect of the assistant metal and platinum may be optimized to thus increase the yield of propylene and to thus improve the long-term operating performance of the catalyst through the reduction of coke formation. Furthermore, the acidity amount of the catalyst is controlled within a predetermined range, and thus it is possible to prevent coke formation from increasing rapidly when the hydrogen/hydrocarbon ratio in a hydrocarbon dehydrogenation reaction is reduced, so that it is possible to operate the process under conditions in which the hydrogen/hydrocarbon ratio is reduced and thus the productivity of the process can be increased, thereby improving the economy of the process.

Another aspect of the present invention is directed to a method for dehydrogenating a hydrocarbon, including the step of bringing the hydrocarbon into contact with a dehydrogenation catalyst in which a platinum-group metal, an assistant metal, and an alkali metal or alkaline earth metal component are supported on a carrier, wherein the molar ratio of platinum to the assistant metal is 0.5 to 1.49, and the catalyst has an acidity amount of 20 to 150 µmol KOH/g catalyst when it is titrated with KOH.

The method of the present invention may be applied for the dehydrogenation of linear hydrocarbons, such as ethane, propane, n-butane, pentane, hexane, heptane or octane. For example, the method of the present invention may be used as a process of producing propylene by dehydrogenation of propane, but is not necessarily limited to this process.

The method for dehydrogenating the hydrocarbon according to the present invention shows little decrease in the performance of the catalyst even under severe reaction conditions, and shows improved effects in terms of the long-term use stability even when the catalyst is severely deactivated. When propane is dehydrogenated at high temperatures in the presence of the dehydrogenation catalyst of the present invention, the catalyst may increase the conversion of propane, the selectivity to propylene as a product, and the yield of propylene.

The present invention will be described in further detail below with reference to examples. However, these examples are merely intended to illustrate specific embodiments, and the scope of the present invention is not limited by these examples.

EXAMPLES

Preparation Examples of Dehydrogenation Catalyst

Spherical alumina having gamma-crystallinity, prepared according to U.S. Pat. No. 4,542,113, was thermally deformed in a tubular electric furnace (available from Korea Furnace) at 1060° C. for 6 hours at an air flow rate of 300 mL/min, and then used as a catalyst carrier. The crystallinity of the resultant alumina was measured by X-ray analysis. The results of the measurement are shown in FIG. 1, and the alumina had a theta crystallinity of 90% or more.

As can be seen in FIG. 1, the proportion of theta phase alumina in the catalyst changed with the change in the thermal deformation temperature of the catalyst. The ratio of alumina phases in the catalyst was controlled by appropriately controlling the thermal deformation temperature and time.

Using the thermally deformed alumina carrier, a catalyst was prepared by room temperature/elevated temperature adsorption. Specifically, 0.0717 g of tin chloride ($SnCl_2$, >99%, Sigma), 0.5714 g of hydrochloric acid (HCl, >35%, JUNSEI), and 0.0714 g of nitric acid ($HNO_3$, 70%, Yakuri) were dissolved in 24 g of distilled water, and then supported on 20 g of the thermally deformed alumina. The supported solution was dried using a rotary evaporator (HAHNSHIN Scientific Co.), stirred at 25 rpm at room temperature for 1.5 hours, and then dried by spinning at 25 rpm under reduced pressure at 80° C. for 1.5 hours. For complete drying, it was dried in an oven at 105° C. for 15 hours, and heat-treated in a heating furnace at 700° C. for 3 hours. Subsequently, 15 g of the tin-supported alumina was added to a solution of 0.3319 g of chloroplatinic acid ($H_2PtCl_6 \cdot 6H_2O$, 99.95%, Aldrich), 0.2143 g of hydrochloric acid and 0.0536 g of nitric acid in 18.0552 g of distilled water so that the solution was supported on the alumina. The supported solution was dried using a rotary evaporator, stirred at 25 rpm at room temperature for 1.5 hours, and then dried by spinning at 25 rpm under reduced pressure at 80° C. for 1.5 hours. It was further dried in an oven at 105° C. for 15 hours, and heat-treated in a heating furnace at 600° C. for 3 hours. Subsequently, 10 g of the tin/platinum-supported alumina was added to a solution of 0.1933 g of potassium nitrate ($KNO_3$, >99%, Sigma-Aldrich) and 0.1629 g of hydrochloric acid in 12.1136 g of distilled water so that the solution was supported on the alumina. The supported solution was dried using a rotary evaporator, stirred at 25 rpm at room temperature for 1.5 hours, and then dried by spinning at 25 rpm under reduced pressure at 80° C. It was further dried in an oven at 105° C. for 15 hours, and heat-treated in a heating furnace at 600° C. for 3 hours, thereby preparing a dehydrogenation catalyst.

Using alumina carriers having different physical properties (molar ratio of platinum to the assistant metal, and acidity amount) as shown in Table 1 below, catalysts were prepared according to the above-described preparation method.

During catalyst preparation, the acidity amount of the catalyst was controlled by controlling the thermal deformation temperature and time or controlling the contents of the assistant metal and the alkali metal or alkaline earth metal.

Examples 1 to 14

As shown in Table 1 below, various dehydrogenation catalysts were prepared in which the molar ratio of platinum to the assistant metal or the acidity amount is included in the scope of the present invention.

Comparative Examples 1 to 4

As shown in Table 1 below, dehydrogenation catalysts were prepared in which the molar ratio of platinum to the assistant metal or the acidity amount was not within the scope of the present invention.

Comparative Examples 5 to 8

As shown in Table 2 below, dehydrogenation catalysts were prepared to thus have different acidity amounts by changing the thermal deformation temperature among the conditions for preparation of the catalysts in which the molar ratio of platinum to the assistant metal was not within the scope of the present invention.

[Method for Evaluation of Catalyst Performance]

The performance of the dehydrogenation catalyst according to the present invention was evaluated according to the following method. 3.2 mL of each of the catalysts prepared in Examples 1 to 14 and Comparative Examples 1 to 8 was packed into a 7 mL quartz reactor, and a gas mixture of propane and hydrogen was fed to each reactor, and a dehydrogenation reaction was performed. The dehydrogenation reaction was performed under adiabatic conditions while the ratio of hydrogen and propane was maintained within the range of 0.2 to 0.5:1 and the following conditions were maintained: a reaction temperature of 620° C.; an absolute pressure of 1.5 atm; and a liquid hourly space velocity (LHSV) of 15 hr$^{-1}$. After the reaction, the gas composition was analyzed using a gas chromatography connected to the reactor, and the conversion of propane, the selectivity for propylene in the reaction product, and the yield of propylene were measured.

Test Example 1: Test for Performance of Dehydrogenation Catalysts with Different Platinum Molar Ratios While the molar ratio of platinum to the assistant metal (tin) was changed, a dehydrogenation reaction was performed according to the procedure described in the "Method for Evaluation of Catalyst Performance" above, and selectivity, conversion and yield were measured. The results of the measurement are shown in Table 1 below:

TABLE 1

| | unit | Examples | | | | | | Comparative Examples | | | |
| --- | --- | --- | --- | --- | --- | --- | --- | --- | --- | --- | --- |
| | | 1 | 2 | 3 | 4 | 5 | 6 | 1 | 2 | 3 | 4 |
| Pt | wt % | 0.5 | 0.5 | 0.5 | 0.5 | 0.5 | 0.5 | 0.5 | 0.5 | 0.5 | 0.5 |
| Sn | wt % | 0.61 | 0.44 | 0.28 | 0.22 | 0.28 | 0.24 | 0.76 | 0.19 | 0.76 | 0.19 |
| K | wt % | 0.85 | 0.85 | 0.85 | 0.85 | 0.85 | 0.8 | 0.85 | 0.85 | 0.85 | 0.85 |
| H$_2$/HC | | 0.5 | 0.5 | 0.5 | 0.5 | 0.2 | 0.2 | 0.5 | 0.5 | 0.2 | 0.2 |
| Reaction pressure | kgf/cm$^2$ | 0.5 | 0.5 | 0.5 | 0.5 | 0.5 | 0.5 | 0.5 | 0.5 | 0.5 | 0.5 |
| LHSV | h$^{-1}$ | 15 | 15 | 15 | 15 | 15 | 15 | 15 | 15 | 15 | 15 |
| Reaction temperature | ° C. | 620 | 620 | 620 | 620 | 620 | 620 | 620 | 620 | 620 | 620 |
| Molar ratio of platinum | | 0.5 | 0.7 | 1.1 | 1.4 | 1.1 | 1.3 | 0.4 | 1.6 | 0.4 | 1.6 |
| Acidity amount | μmol/KOH/g | 20 | 34 | 78 | 104 | 78 | 93 | 28 | 124 | 28 | 124 |
| Bulk density | g/cc | 0.75 | 0.75 | 0.75 | 0.75 | 0.75 | 0.75 | 0.75 | 0.75 | 0.75 | 0.75 |
| Specific surface area | m$^2$/g | 88 | 85 | 89 | 87 | 89 | 91 | 82 | 90 | 82 | 90 |
| Thermal deformation temperature | ° C. | 1060 | 1060 | 1060 | 1060 | 1060 | 1060 | 1060 | 1060 | 1060 | 1060 |
| Conversion | % | 33.7 | 34 | 35.4 | 35.2 | 37.8 | 37.2 | 30.6 | 33.4 | 32.7 | 35.2 |
| Selectivity | % | 94.6 | 94.8 | 95 | 95.1 | 95.2 | 95.3 | 94 | 94.5 | 94.7 | 95 |
| Yield | % | 31.9 | 32.2 | 33.6 | 33.5 | 36 | 35.5 | 28.8 | 31.6 | 31 | 33.4 |
| Content of coke | wt % | 2.5 | 2.7 | 3.8 | 4.5 | 5.3 | 6.5 | 2.2 | 4.7 | 4.1 | 9.7 |

As can be seen from the results in Table 1 above, when the molar ratio of platinum to the assistant metal was changed while the content of platinum was maintained at a constant level and the content of the assistant metal tin was changed, it could be seen that the catalysts according to the present invention achieved higher propane conversion, selectivity and process yield compared to the catalyst of the conventional art. In particular, in the case of the catalyst of Comparative Example 1 in which the molar ratio of platinum to the assistant metal was 0.4, tin covered the surface of platinum due to an excessive amount of tin compared to that in the catalysts of the present invention (Examples 1 to 4) to thus reduce the exposed platinum area onto which propane could be adsorbed, thereby reducing the activity of the catalyst. Meanwhile, in the case of the catalyst of Comparative Example 2 in which the molar ratio of platinum to the assistant metal was 1.6, coke formation on the catalyst increased with the passage of reaction time compared to the catalysts of the present invention (Examples 1 to 4), and the effect of increasing the activity of the catalyst was reduced due to the deactivation of the catalyst, and thus the activity of the catalyst was reduced rapidly. Furthermore, in the case where the molar ratio of platinum to the assistant metal was between 0.5 and less than 1.49, coke formation on the catalyst was inhibited in the catalysts of the present invention (Examples 5 to 6) compared to Comparative Example 4 even under an operating condition in which the hydrogen/propane (H$_2$/HC) ratio was 0.2, at which coke formation on the catalyst would increase rapidly. This indicates that the performance of the catalyst of the present invention was improved compared to that of conventional catalysts. In the case of Comparative Example 3, under an operating condition in which the hydrogen/propane (H$_2$/HC) ratio was 0.2, the activity of platinum was reduced due to tin as supported in a larger amount than that in the catalysts of the present invention (Examples 5 to 6), and thus the performance of the catalyst was reduced.

Test Example 2: Test for Performance of Dehydrogenation Catalysts with Different Acidity Amounts Using the catalysts of Example 7 to 14 and the catalysts of Comparative Examples 5 to 8, which had different acidity amounts, a dehydrogenation reaction was performed under the reaction conditions shown in Table 2 below according to the procedure described in the "Method for Evaluation of Catalyst Performance" above, and selectivity, conversion and yield were measured. The results of the measurement are shown in Table 2 below:

and a high propylene yield in the propane dehydrogenation reaction, suggesting that it had a very high catalytic activity.

Although the preferred embodiments of the present invention have been described in detail above, the descriptions have been given for illustrative purposes only. It will be understood by a person having ordinary knowledge in the art to which the present invention pertains that various modifications, alterations, additions, etc. may be possible without departing from the spirit and scope of the invention. These modifications, alterations, etc. should be understood as falling within the range of protection of the present invention.

The invention claimed is:

1. A dehydrogenation catalyst comprising:
   a platinum-group metal;
   an assistant metal; and
   an alkali metal or alkaline-earth metal component,
   the platinum-group metal, the assistant metal, and the alkali metal or alkaline-earth metal component being supported on a carrier, wherein
   a molar ratio of platinum to the assistant metal is 0.5 to 1.49, and
   an acidity amount of 20 to 150 μmol KOH/g catalyst is obtained, which is determined by titration of the catalyst with KOH.

TABLE 2

| | unit | Examples | | | | | | | | Comparative Examples | | | |
|---|---|---|---|---|---|---|---|---|---|---|---|---|---|
| | | 7 | 8 | 9 | 10 | 11 | 12 | 13 | 14 | 5 | 6 | 7 | 8 |
| Pt | wt % | 0.5 | 0.5 | 0.5 | 0.4 | 0.5 | 0.5 | 0.5 | 0.5 | 0.5 | 0.4 | 0.5 | 0.4 |
| Sn | wt % | 0.44 | 0.28 | 0.28 | 0.2 | 0.32 | 0.21 | 0.28 | 0.32 | 0.65 | 0.15 | 0.65 | 0.15 |
| K | wt % | 0.85 | 0.85 | 0.85 | 0.7 | 0.7 | 0.4 | 0.85 | 0.7 | 0.85 | 1 | 0.85 | 1 |
| H$_2$/HC | | 0.5 | 0.5 | 0.5 | 0.5 | 0.5 | 0.5 | 0.2 | 0.2 | 0.5 | 0.5 | 0.2 | 0.2 |
| Reaction pressure | kgf/cm$^2$ | 0.5 | 0.5 | 0.5 | 0.5 | 0.5 | 0.5 | 0.5 | 0.5 | 0.5 | 0.5 | 0.5 | 0.5 |
| LHSV | h$^{-1}$ | 15 | 15 | 15 | 15 | 15 | 15 | 15 | 15 | 15 | 15 | 15 | 15 |
| Reaction temperature | ° C. | 620 | 620 | 620 | 620 | 620 | 620 | 620 | 620 | 620 | 620 | 620 | 620 |
| Molar ratio of platinum | | 0.7 | 1.1 | 1.1 | 1.2 | 1 | 1.45 | 1.1 | 1 | 0.47 | 1.6 | 0.47 | 1.6 |
| Acidity amount | μmol/KOH/g | 21 | 78 | 113 | 124 | 68 | 150 | 78 | 68 | 14 | 155 | 14 | 155 |
| Bulk density | g/cc | 0.83 | 0.75 | 0.65 | 0.75 | 0.75 | 0.6 | 0.75 | 0.75 | 0.85 | 0.63 | 0.85 | 0.63 |
| Specific surface area | m$^2$/g | 69 | 89 | 110 | 85 | 86 | 1030 | 89 | 86 | 63 | 108 | 63 | 108 |
| Thermal deformation temperature | ° C. | 1080 | 1060 | 1040 | 1060 | 1060 | 1060 | 1060 | 1060 | 1085 | 1030 | 1085 | 1030 |
| Conversion | % | 31.5 | 35.4 | 34.2 | 32.1 | 34.8 | 29.6 | 37.8 | 37.3 | 30.7 | 29.5 | 32.4 | 27.1 |
| Selectivity | % | 94 | 95 | 94.8 | 94.2 | 94.9 | 93.7 | 95.2 | 95.1 | 94.1 | 93.7 | 94.4 | 90.7 |
| Yield | % | 29.6 | 33.6 | 32.4 | 30.2 | 33 | 27.7 | 36 | 35.5 | 28.9 | 27.6 | 30.6 | 24.6 |
| Content of coke | wt % | 1.7 | 3.8 | 4.7 | 5 | 3.2 | 6.9 | 5.3 | 4.9 | 1.1 | 7.3 | 3.5 | 18.2 |

As can be seen from the results in Table 2 above, when the acidity amount was within the scope of the present invention, the process yield could be improved because the dehydrogenation process could be carried out even under a condition in which the hydrogen/hydrocarbon (H$_2$/HC) ratio was reduced. Furthermore, the dehydrogenation reaction was carried out using the inventive catalyst having a controlled acidity amount, and as a result, it was shown that the catalyst showed a high propane conversion, a high selectivity for propylene in the product, and a high propylene yield, indicating that the catalyst had a very high activity. Accordingly, it can be seen that the dehydrogenation catalyst according to the present invention exhibited a high propane conversion, a high selectivity for propylene in the product, 2. The dehydrogenation catalyst of claim 1, wherein the catalyst comprises, based on the total weight of the catalyst, 0.3 to 0.8 wt % of platinum and 0.4 to 0.9 wt % of the alkali metal or alkaline-earth metal.

3. The dehydrogenation catalyst of claim 1, wherein the catalyst has a bulk density of 0.55 to 0.9 g/cc.

4. The dehydrogenation catalyst of claim 1, wherein the catalyst has a pill size of 1.2 to 2.5 mm.

5. The dehydrogenation catalyst of claim 1, wherein the carrier comprises both mesopores having an average pore size of 5 to 100 nm and a total pore volume of 0.05 to 2 cm$^3$/g and macropores having an average pore size of 0.1 to 20 μm and a total pore volume of 0.05 to 3 cm$^3$/g.

6. The dehydrogenation catalyst of claim 1, wherein the alkali metal or alkaline-earth metal is one or more selected from the group consisting of calcium, potassium, sodium, magnesium, lithium, strontium, barium, radium, and beryllium.

7. The dehydrogenation catalyst of claim 1, wherein the assistant metal is one or more selected from the group consisting of tin, germanium, gallium, indium, zinc, and manganese.

8. The dehydrogenation catalyst of claim 1, wherein the carrier is selected from the group consisting of $TiO_2$, $SiO_2$, $Al_2O_3$, $ZrO_2$, $Cr_2O_3$, $Nb_2O_5$, and mixtures thereof.

9. The dehydrogenation catalyst of claim 8, wherein the alumina ($Al_2O_3$) carrier comprises 90% to 100% theta-crystalline phase and 0% to 10% alpha-crystalline phase or gamma-crystalline phase.

10. The dehydrogenation catalyst of claim 1, wherein the carrier has a specific surface area of 50 to 170 $m^2/g$.

11. The dehydrogenation catalyst of claim 1, wherein the catalyst further comprises one or more halogen components selected from the group consisting of chlorine, phosphorus, and fluorine.

12. A method for dehydrogenating a hydrocarbon, the method comprising bringing the hydrocarbon into contact with a dehydrogenation catalyst set forth in claim 1.

13. The method of claim 12, wherein the hydrocarbon is one selected from the group consisting of ethane, propane, n-butane, pentane, hexane, heptane, and octane.

* * * * *